United States Patent
Barkholt et al.

(10) Patent No.: US 9,254,229 B2
(45) Date of Patent: Feb. 9, 2016

(54) PACKAGING UNIT AND A DISPENSER FOR DISPOSABLE ARTICLES

(75) Inventors: Bo Winther Barkholt, Glamsbjerg (DK); Poul Bertelsen, Assens (DK); Flemming Buch, Odense (DK); Karsten Plum, Assens (DK)

(73) Assignee: PLUM A/S, Assens (DK)

( * ) Notice: Subject to any disclaimer, the term of this patent is extended or adjusted under 35 U.S.C. 154(b) by 1197 days.

(21) Appl. No.: 12/304,079

(22) PCT Filed: Feb. 28, 2007

(86) PCT No.: PCT/DK2007/000097
§ 371 (c)(1),
(2), (4) Date: Dec. 9, 2008

(87) PCT Pub. No.: WO2007/140772
PCT Pub. Date: Dec. 13, 2007

(65) Prior Publication Data
US 2009/0200192 A1  Aug. 13, 2009

(30) Foreign Application Priority Data
Jun. 9, 2006 (DK) ................................. 2006 00786

(51) Int. Cl.
*A61B 19/00* (2006.01)
*A61F 15/00* (2006.01)

(52) U.S. Cl.
CPC .................................... *A61F 15/002* (2013.01)

(58) Field of Classification Search
CPC ... A61F 15/002; A61F 15/003; A61F 15/001; A61F 15/00; B65D 83/08; A47F 1/00; A47F 1/08
USPC ......... 206/440, 438, 441, 233, 820, 525, 472, 206/474, 528; 221/305, 306, 46, 49, 92, 221/191, 197, 281, 282, 283, 287; 229/87.01, 87.05
See application file for complete search history.

(56) References Cited

U.S. PATENT DOCUMENTS 3,384,291 A * 5/1968 Graser ........................... 206/434
3,589,555 A * 6/1971 Burkhalter, Jr. ................ 221/35
(Continued)

FOREIGN PATENT DOCUMENTS

| EP | 073357 A2 | 9/1996 |
|----|-----------|--------|
| GB | 2018228 A | 10/1979 |
| WO | WO-2004/000688 A1 | 12/2003 |

*Primary Examiner* — Andrew Perreault
(74) *Attorney, Agent, or Firm* — Muncy, Geissler, Olds & Lowe, P.C.

(57) ABSTRACT

A packaging unit for holding a plurality of articles, preferably disposable articles, such, as plasters, tissues, gauze, etc. The packaging unit comprises a holding member (2) comprising a first part (5) with at most fifteen spaced apart flaps (6), and a second part (7), the first and second parts being arranged oppositely each other. A plurality of articles are arranged and retained between the first and second parts in such a manner that an individual article can be removed from the packaging unit. The packaging unit is insertable in a dispenser (13) and may serve as a refill package. Furthermore, a dispenser for delivering disposable articles, the dispenser comprising a retaining part (14) for retaining a packaging unit and an opening (15) allowing a packaging unit to be inserted and allowing an individual article to be delivered. The opening is arranged in such a manner that an individual article may be delivered from the dispenser by pulling it in a substantially downwards direction. The dispenser improves the hygienic standard as compared to prior art dispensers because the position of the opening prevents dirt, blood, or various items from entering the dispenser due to the force of gravity, thereby contaminating the articles positioned in the dispenser.

9 Claims, 4 Drawing Sheets

(56) References Cited

U.S. PATENT DOCUMENTS

| | | | | |
|---|---|---|---|---|
| 4,194,624 | A | * | 3/1980 | Spiegelberg ............... 206/441 |
| 4,398,631 | A | * | 8/1983 | Graser ....................... 206/427 |
| 4,850,511 | A | * | 7/1989 | Kral et al. ................. 221/306 |
| 5,096,089 | A | | 3/1992 | McLaughlin |
| 5,927,543 | A | | 7/1999 | Dejardin et al. |
| 6,050,413 | A | * | 4/2000 | Benedetti ................... 206/440 |
| 6,708,841 | B2 | * | 3/2004 | Baughman ................. 221/46 |
| 2004/0004014 | A1 | | 1/2004 | Grossman |
| 2005/0017059 | A1 | | 1/2005 | Salani et al. |

* cited by examiner

PACKAGING UNIT AND A DISPENSER FOR DISPOSABLE ARTICLES

FIELD OF THE INVENTION

The present invention relates to a packaging unit for holding a plurality of articles, preferably disposable articles, such as plasters, cleansing tissues, disinfection tissues, etc. The present invention further relates to a dispenser for delivering disposable articles. The packaging unit according to the invention can preferably be inserted in the dispenser according to the invention, the articles being held by the packaging unit thereby being delivered via the dispenser.

BACKGROUND OF THE INVENTION

Various dispensers for delivering disposable articles, such as plasters, cleansing tissues, etc., are known in the art. It is also known to design such dispensers in manner which allows them to be refilled, i.e. a new packaging unit with a number of disposable articles can be positioned in the dispenser, replacing an empty packaging unit.

One example of such a refillable dispenser is manufactured by Cederroth AB. The dispenser is provided with a body part defining an opening and a lid part covering the opening. Inside the body part two packaging units, each holding a plurality of plasters, can be accommodated. The packaging units are retained by the body part in such a manner that when a person pulls an individual plaster, that individual plaster is removed from the dispenser through an opening while the packaging unit as well as the remaining plasters of the packaging unit remain in the dispenser. Furthermore, part of the wrapping of the removed plaster also remains in the dispenser. Thereby a sticky part of the removed plaster is exposed, and the plaster will be ready for use, i.e. it can readily be positioned across a wound.

The opening defined in the body part of the dispenser is arranged in such a manner that the plasters must be pulled in an upwards direction in order to remove them from the dispenser. This is a disadvantage because thereby dirt and possibly blood dripping from a wound may enter the interior of the body part where the plasters are stored. Thereby the plasters may be contaminated, and it is difficult to maintain a desired hygienic standard in the dispenser.

SUMMARY OF THE INVENTION

It is, thus, an object of the invention to provide a dispenser for delivering disposable articles, in which the hygienic standard is increased as compared to prior art dispensers.

It is a further object of the invention to provide a dispenser for delivering disposable articles, in which contamination of the disposable articles is reduced to a minimum.

It is an even further object of the invention to provide a packaging unit for holding a plurality of disposable articles, where the packaging unit can be inserted in a dispenser with an increased hygienic standard.

According to a first aspect of the invention the above and other objects are fulfilled by providing a packaging unit for holding a plurality of articles, said packaging unit comprising:

a holding member comprising a first part with at most fifteen spaced apart flaps and a second part, the holding member being foldable along a folding line in such a manner that the first part and the second part are arranged opposite to each other, and a plurality of articles being arranged and retained between the first part and the second part in such a manner that an individual article can be removed from the packaging unit.

The first part comprises at most fifteen spaced apart flaps. Thereby the holding member may be fitted into a dispenser having protruding parts arranged at positions corresponding to at least some of the spacings between the flaps. At the same time the flaps may abut another part of the dispenser. This allows the packaging unit to be securely fitted, in multiple directions, into such a dispenser in a manner which allows an individual article to be removed from the packaging unit without risking that the entire packaging unit is removed from the dispenser. This is an advantage.

The first part may comprise a lower number of spaced apart flaps, such as ten, five, four, three, etc. Preferably, the number of spaced apart flaps is dividable by five in order to allow the packaging unit to be securely fitted into a matching dispenser as described above.

When the holding member is folded along the folding line the result is that the first part and the second part are arranged opposite to each other, i.e. defining a space there between. Thereby the plurality of articles can be arranged between the first part and the second part in the defined space. The articles are retained between the first part and the second part. Thus, the articles are held by the holding member in such a manner that a force must be applied to remove an article. This may be achieved by fixing the first part, the second part and the articles arranged there between relatively to each other, e.g. by stapling the parts together. However, it should be ensured that the articles are fixed to the first and second parts in a manner which allows an individual article to be removed from the packaging unit without damaging the article or the packaging unit. This may, e.g., be achieved by providing the articles with a detachable part which is fixed to the holding member in such a manner that the detachable part remains fixed to the holding member while the remaining part of the article is removed. This will be described further below. It should be understood that when an individual article is removed from the packaging unit, only that particular article is removed, while any other article of the packaging will remain retained in the packaging unit.

The holding member is preferably folded along the folding line at a manufacturing site, the articles subsequently or simultaneously being arranged and fixed between the first and second parts as described above.

The second part may have at most six spaced apart flaps. The second part may comprise a smaller number of spaced apart flaps, such as three, two, etc. Preferably, the number of spaced apart flaps of the second part is dividable by three. According to this embodiment the holding member may be fitted into a dispenser having protruding parts arranged at positions corresponding to the spacings between the flaps of the second part. Thereby the packaging unit may be fitted even more securely into the dispenser for the reasons described above.

According to a preferred embodiment the first part may have five spaced apart flaps and/or the second part may have three spaced apart flaps.

The flaps of the first part may have at least substantially the same size in a direction defined by the folding line. When the packaging unit is arranged in a dispenser in such a manner that the flaps of the first part abuts a part of the dispenser, a force will be applied to the flaps of the first part when an article is removed from the packaging unit, because the abutment ensures that the packaging unit remains in the dispenser. When the flaps have at least substantially the same size in a direction defined by the folding line, i.e. the flaps have at least substantially the same width, the load arising from this force will be at least substantially equally distributed across the first part. The resulting construction is, thus, very stabile.

Furthermore, the spacings between the flaps of the first part, along the direction defined by the folding line, may have at least substantially the same size as the size of the flaps of the first part along said direction. Thereby an even more stabile construction is provided.

The articles are preferably disposable articles. Thus, the articles may advantageously be individually wrapped plasters. Alternatively, the articles may be cleansing tissues, disinfection tissues, gauze, or any other suitable kind of disposable articles.

In the case that the articles are individually wrapped plasters, part of the wrapping may be left in the packaging unit when an individual plaster is removed from the packaging unit. The part remaining in the packaging unit may advantageously be a part which covers a sticky part of the plaster. In this case the plaster will be ready for use as soon as it has been removed from the packaging unit, i.e. it may immediately be applied to a wound, and removing the plaster and applying it to a wound may even be done using only one hand.

The holding member may be made from cardboard. This is an advantage because cardboard is non-expensive and easily foldable. Furthermore, a holding member of a desired shape may easily be cut from a sheet of cardboard. Finally, cardboard is recyclable and thereby environment friendly.

Alternatively, the holding member may be made from another suitable material, which is foldable while being sufficiently rigid to allow the packaging unit to be fitted securely into a dispenser, e.g. a suitable plastic material, such polypropylene (PP).

The perpendicular distance from the folding line to an edge of the first part may be within the interval from 50 mm to 80 mm, such as within the interval from 60 mm to 70 mm, such as approximately 65 mm. In the present context the term 'perpendicular distance' should be interpreted to mean the distance along a direction being at least substantially perpendicular to the folding line. 'The perpendicular distance' should be interpreted as a representative distance along this direction.

Alternatively or additionally, the perpendicular distance from the folding line to an edge of the second part may be within the interval from 20 mm to 50 mm, such as within the interval from 30 mm to 40 mm, such as approximately 35 mm.

According to a second aspect of the invention the above and other objects are fulfilled by providing a dispenser for delivering disposable articles, the dispenser comprising:
a retaining part for retaining a packaging unit holding a plurality of disposable articles,
an opening allowing a packaging unit to be inserted in the dispenser, and allowing an individual disposable article to be delivered from the dispenser,
wherein the opening is arranged in such a manner that an individual disposable article may be delivered from the dispenser by pulling it in a substantially downwards direction.

It should be noted that a person skilled in the art would readily recognise that any feature described in combination with the first aspect of the invention may also be combined with the second aspect of the invention, and vice versa.

The retaining part is adapted to retain a packaging unit holding a plurality of disposable articles. The packaging unit is replaceable, i.e. when all the disposable article of one packaging unit has been used, the empty packaging unit can be removed from the dispenser and another packaging unit holding a plurality of disposable articles can be inserted in the retaining part of the dispenser. Since the packaging unit is retained by the retaining part, it will remain in the dispenser once positioned there, unless it is actively removed. Thus, the packaging unit will not spontaneously fall out of the dispenser.

A packaging unit can be inserted in the dispenser via the opening. Thereby it is very easy to insert a new packaging unit in the dispenser. Furthermore, an individual disposable article can be delivered from the dispenser through the opening. Accordingly, the packaging is preferably positioned in the dispenser in such a manner that the disposable articles at least partly project through the opening.

The opening is arranged in such a manner that an individual article may be delivered from the dispenser by pulling it in an at least substantially downwards direction. In the present context the term 'downwards direction' should be interpreted to mean a direction defined by gravity. Accordingly, the opening is preferably arranged in such a manner that it faces downwards, and it is therefore important that the retaining part prevents the packaging unit from falling out of the dispenser due to the force of gravity acting upon the packaging unit. It is an advantage that the opening is arranged as described above, because it is thereby avoided that dirt and other undesired items enter the dispenser under the influence of the force of gravity. Furthermore, when the disposable articles are plasters, these can be delivered from the dispenser without the risk of dripping blood from a wound into the dispenser and possibly contaminating the remaining plasters in the dispenser. Accordingly, the hygienic standard of the dispenser is increased relatively to prior art dispensers, and the risk of contamination of the disposable articles is considerably reduced. This is a great advantage.

The retaining part may preferably be adapted to retain a packaging unit according to the first aspect of the invention. Thus, the retaining part may comprise first protruding parts adapted to engage with the flaps of the first part of a packaging unit retained by the retaining part, and second protruding parts adapted to engage with the second part of said packaging unit. Such protruding parts should be arranged in such a manner that engagement between the protruding parts and the first/second parts prevents the packaging unit from falling out of the dispenser due to the force of gravity. Accordingly, the protruding parts may preferably be arranged at or near the opening defined in the retaining part.

Furthermore, the retaining part may be provided with protruding parts which are arranged at positions corresponding to positions of spacings between flaps on the first and/or second part of the packaging unit. This has been explained in detail above.

The dispenser may further comprise a lid part arranged opposite the opening, the lid part thereby providing protection for disposable articles contained in the dispenser. Since the lid part is arranged opposite the opening, it preferably faces an upwards direction, thereby providing protection from dirt or items moving under the influence of the force of gravity. The lid part may be movable in such a manner that it is possible to gain access to the interior of the dispenser, e.g. in order to remove and empty packaging unit.

The lid part may be pivotally movable between a first position in which the lid part provides protection for disposable articles contained in the dispenser, and a second position in which access is allowed to the interior of the dispenser. In this case the lid part may further serve as a 'shelf' when it is in the second position.

BRIEF DESCRIPTION OF THE DRAWINGS

The invention will now be described in further detail with reference to the accompanying drawings in which.

DETAILED DESCRIPTION OF THE DRAWINGS

Figure 1:
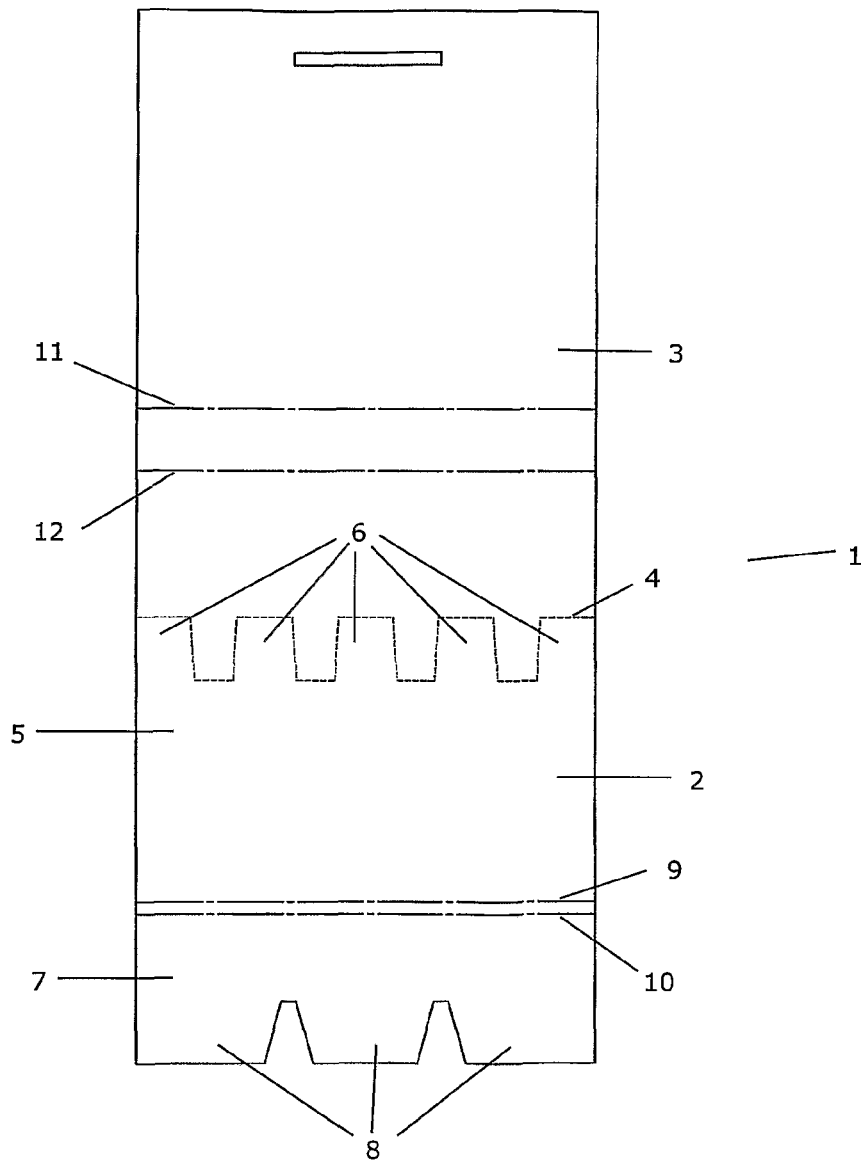
FIG. 1 shows a packaging unit according to an embodiment of the invention.

FIG. 1 shows a sheet of cardboard 1 which can be cut and folded into a packaging unit according to an embodiment of the invention. The cardboard 1 sheet comprises a holding member part 2 and a wrapping part 3 divided by a perforated line 4. The holding member part 2 and the wrapping part 3 may be separated along the perforated line 4.

The holding member part 2 comprises a first part 5 with five spaced apart flaps 6, and a second part 7 with three spaced apart flaps 8. The holding member part 2 is foldable along folding lines 9, 10. When the holding member part 2 is folded along folding lines 9, 10, the first part 5 and the second part 7 will be arranged opposite each other in such a manner that the flaps 6, 8 point in the same direction. Then a plurality of plasters (not shown) can be positioned between the first part 5 and the second part 7, and the parts 5, 7 and the plasters can be fixed relatively to each other, e.g. by stapling them together.

The wrapping part 3 is foldable along folding lines 11, 12. Thus, the wrapping part 3 may be used for enclosing a plurality of plasters retained between the first part 5 and the second part 7, thereby forming a packaging unit. The packaging unit is preferably folded in this manner when it is not inserted in a dispenser, i.e. the packaging unit is preferably folded in this manner when it is delivered as a 'refill' for the dispenser.

When the packaging unit is inserted into a dispenser, the holding member part 2 and the wrapping part 3 are separated along the perforated line 4, thereby exposing the plasters.

Figure 2:
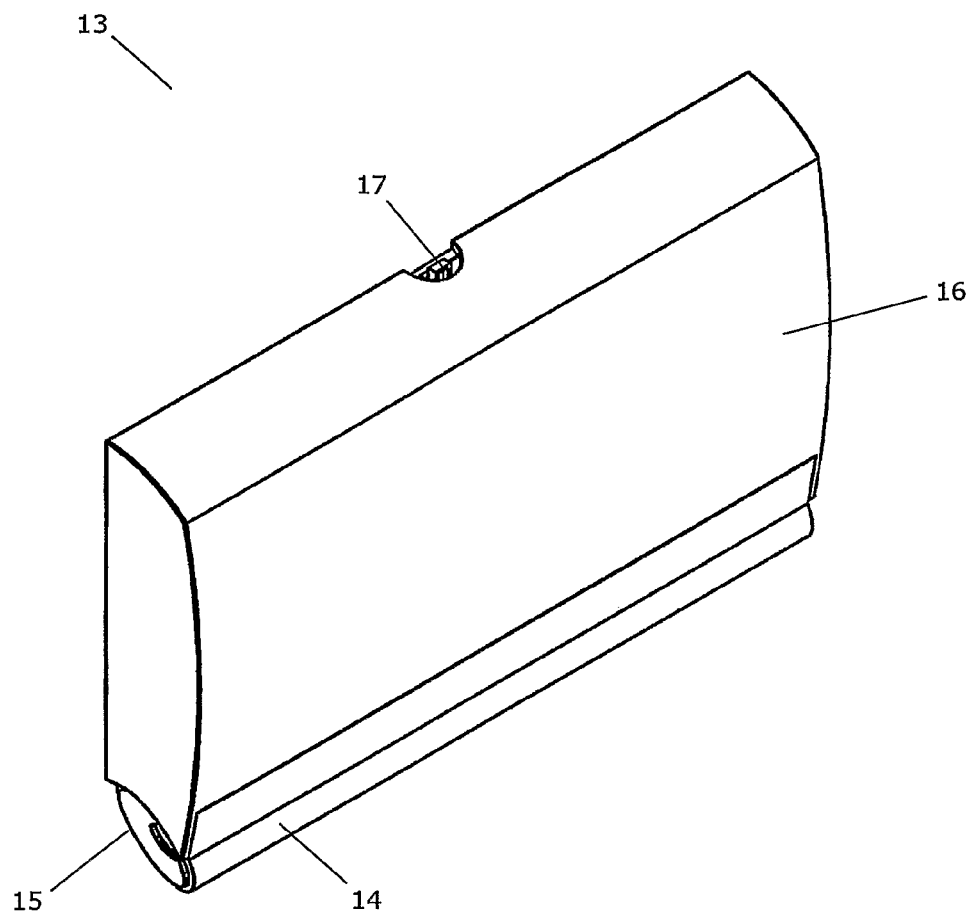
FIG. 2 is a perspective view of a dispenser according to an embodiment of the invention, the dispenser having a lid part in a closed position.

FIG. 2 is a perspective view of a dispenser 13 according to an embodiment of the invention. The dispenser 13 is adapted to deliver plasters. The dispenser 13 comprises a retaining part 14 defining an opening 15 facing downwards. Thus, when a packaging unit is positioned in the dispenser 13 as described above, plasters will project through the opening 15 in a downwards direction. The retaining part 14 is adapted to be mounted on a wall or another at least substantially vertical surface.

The dispenser 13 further comprises a lid part 16 being pivotally mounted on the retaining part 14. In FIG. 2 the lid part 16 is shown in a closed position in which it shields the interior of the dispenser 13 against dirt and items moving under the Influence of the force of gravity. The lid part 16 is maintained in the closed position by means of a manually operable locking member 17.

Figure 3:
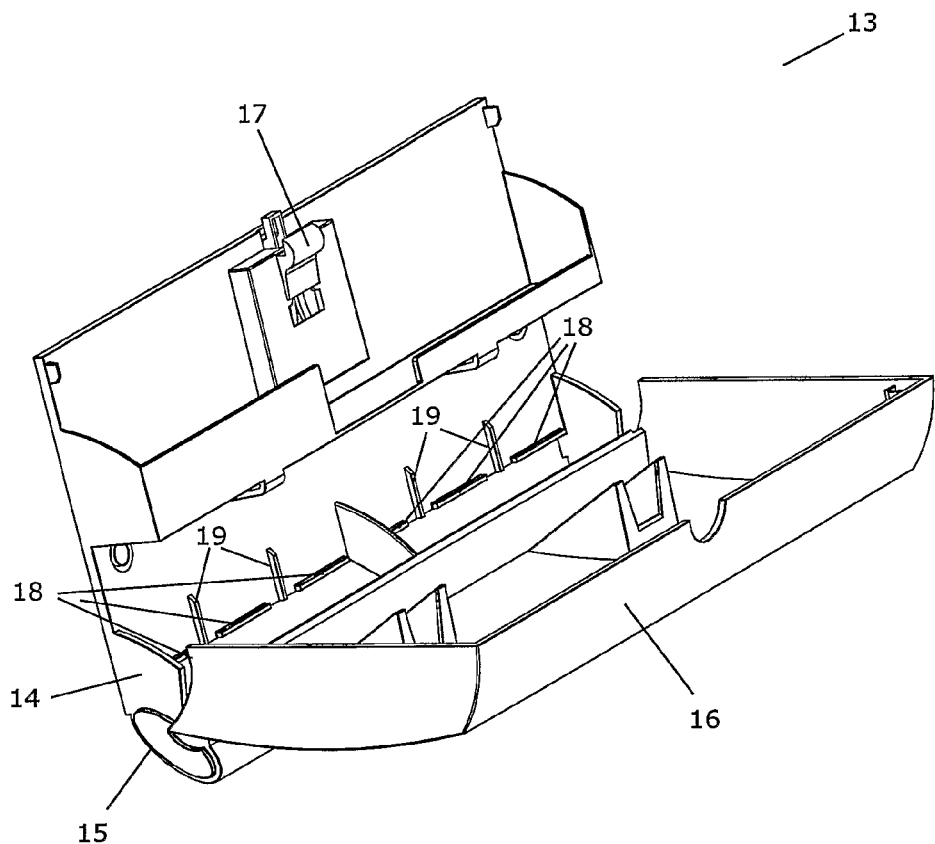
FIG. 3 is a perspective view of the dispenser of FIG. 2 with the lid part in an open position.

FIG. 3 is a perspective view of the dispenser 13 of FIG. 2. However, in FIG. 3 the lid part 16 is in an open position providing access to the interior of the dispenser 13.

Figure 4:
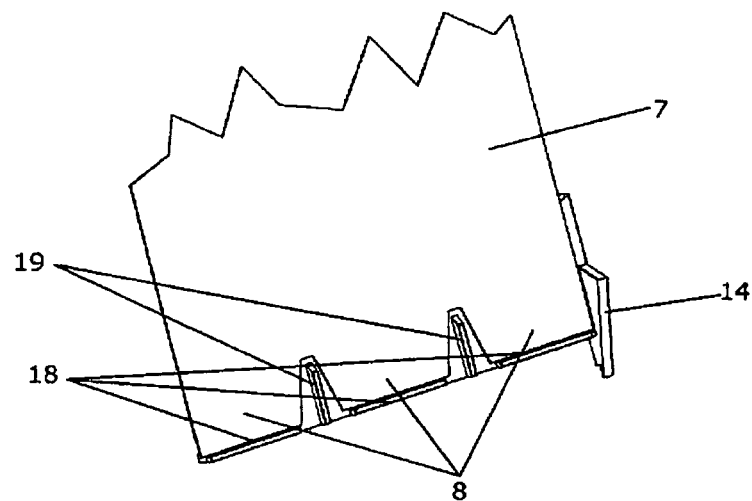
FIG. 4 is a sectional, perspective view showing the first protruding parts engaging with the flaps of the second part of the packaging unit.
Figure 5:
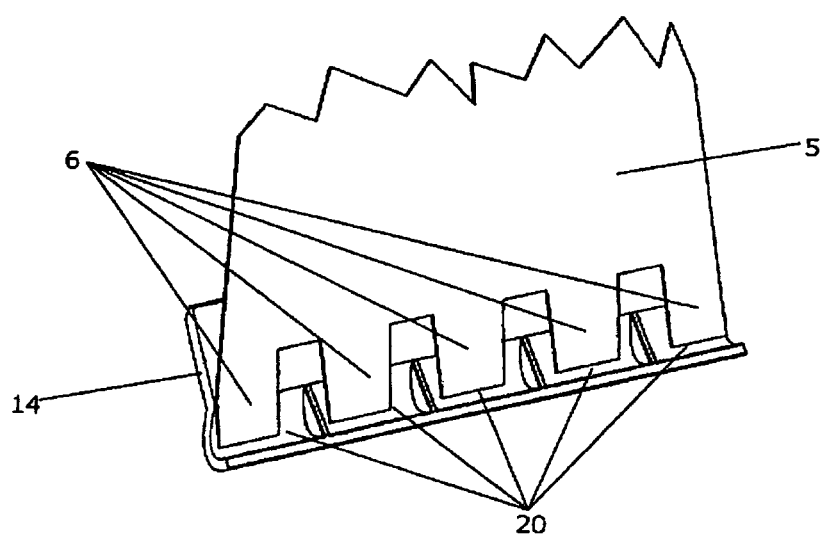
FIG. 5 is a sectional, perspective view showing the second protruding parts engaging with the first part of the packaging unit.

The retaining part 14 can accommodate two packaging units, e.g. of the kind illustrated in FIG. 1. When a packaging unit as illustrated in FIG. 1 is inserted in the retaining part 14 the three flaps 8 of the second part 7 abut protruding parts 18 as seen in FIG. 4. Additional protruding parts 20 in FIG. 5 arranged opposite the protruding parts 18 abut the flaps 6 of the first part 5.

Furthermore, protruding parts 19 are arranged on the retaining part 14 in such a manner that the spacings between the flaps 8 will be positioned exactly at the position of the protruding parts 19. These spacings act as means for receiving the protruding parts 19 of the dispenser 13. Thus, when a packaging unit is inserted in the retaining part 14 it will be securely fitted therein in a vertical as well as a horizontal direction.

A packaging unit can be inserted in the retaining part 14 without moving the lid part 16 to the open position. This is done by introducing the packaging unit through the opening 15 until the flaps 6, 8 have passed protruding parts 18. On the other hand, when an empty packaging unit is to be removed it is necessary to move the lid part 16 to the open position because the engagement between the flaps 6 and the protruding parts 18, and the engagement between the flaps 8 and the additional protruding parts (not visible) prevents the packaging unit from leaving the retaining unit 14 through the opening 15.

When the lid part 16 is in an open position as illustrated in FIG. 3, it may serve as a 'shelf', i.e. it may be used for temporarily positioning various items, such as empty or new packaging units.

The invention claimed is:

1. A packaging unit for holding a plurality of articles, said packaging unit comprising:
   a holding member comprising a first part and a second part, the second part having at least three and at most fifteen spaced apart flaps, thereby defining, between the flaps, means for receiving protruding parts of a dispenser, the holding member being foldable along a folding line in such a manner that the first part and the second part are arranged opposite to each other,
   the first part and the second part being adapted to retain a plurality of articles between them in such a manner that an individual article can be removed from the packaging unit, and
   a wrapping part divided from the holding member by a perforated line, said perforated line allowing the wrapping part to be separated from the holding part along the perforated line,
   wherein the perforated line extends continuously from one edge to another edge of the packaging unit, and wherein the wrapping part and the holding part are without openeings adjacent the perforated line.

2. The packaging unit according to claim 1, wherein the second part has at most six spaced apart flaps.

3. The packaging unit according to claim 1, wherein the first part has five spaced apart flaps and/or the second part has three spaced apart flaps.

4. The packaging unit according to claim 1, wherein the perpendicular distance from the folding line to an edge of the first part is within the interval from 50 mm to 80 mm.

5. The packaging unit according to claim 1, wherein the perpendicular distance from the folding line to an edge of the second part is within the interval from 20 mm to 50 mm.

6. A dispenser for delivering disposable articles and packaging unit combination, the dispenser and packaging unit combination comprising:

a retaining part in the dispenser adapted to retain a packaging unit, said packaging unit being adapted to hold a plurality of disposable articles, the packaging unit having a holding member comprising a first part and a second part, the second part having at least three and at most fifteen spaced apart flaps, thereby defining, between the flaps, means for receiving protruding parts of a dispenser, the holding member being foldable along a folding line in such a manner that the first part and the second part are arranged opposite to each other, and the first part and the second part being adapted to retain a plurality of articles between them in such a manner that an individual article can be removed from the packaging unit, the retaining part comprising the protruding parts of the dispenser which include first protruding parts engaging with the flaps of the second part of the packaging unit when the packaging unit is retained by the retaining part, and second protruding parts engage with the first part of said packaging unit, an opening in the dispenser allowing a packaging unit to be inserted in the dispenser, and allowing an individual disposable article to be delivered from the dispenser, wherein the opening is arranged in such a manner that an individual disposable article may be delivered from the dispenser by pulling it in a substantially downwards direction.

7. The dispenser and packaging unit combination according to claim 6, wherein the retaining part is provided with protruding parts arranged at positions corresponding to positions of spacings between flaps on the first part of the packaging unit.

8. The dispenser and packaging unit combination according to claim 6, wherein the perpendicular distance from the folding line of the packaging unit to an edge of the first part of the packaging unit is within the interval from 50 mm to 80 mm.

9. The dispenser and packaging unit combination according to claim 6, wherein the perpendicular distance from the folding line of the packaging unit to an edge of the second part of the packaging unit is within the interval from 20 mm to 50 mm.

* * * * *